United States Patent
Marlowe et al.

(10) Patent No.: US 9,125,405 B2
(45) Date of Patent: *Sep. 8, 2015

(54) CONTACT LENS SOLUTION WITH A TERTIARY AMINE OXIDE

(75) Inventors: Zora Marlowe, Rochester, NY (US); Hongna Wang, Ontario, NY (US); Susan E. Burke, Batavia, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 1498 days.

This patent is subject to a terminal disclaimer.

(21) Appl. No.: 12/574,732

(22) Filed: Oct. 7, 2009

(65) Prior Publication Data

US 2010/0104528 A1    Apr. 29, 2010

Related U.S. Application Data

(60) Provisional application No. 61/108,920, filed on Oct. 28, 2008.

(51) Int. Cl.
*A61K 31/16* (2006.01)
*A01N 33/16* (2006.01)

(52) U.S. Cl.
CPC ...................................... *A01N 33/16* (2013.01)

(58) Field of Classification Search
CPC .............................. A61K 31/51; A61K 31/16
See application file for complete search history.

(56) References Cited

U.S. PATENT DOCUMENTS

| | | | |
|---|---|---|---|
| 5,765,579 A * | 6/1998 | Heiler et al. ................ | 134/42 |
| 5,840,671 A | 11/1998 | Fujimura et al. | |
| 6,063,745 A * | 5/2000 | Graham et al. ............. | 510/112 |
| 6,479,454 B1 | 11/2002 | Smith et al. | |
| 6,565,894 B1 * | 5/2003 | Smith et al. ................ | 424/616 |
| 2002/0039975 A1 * | 4/2002 | Stone et al. ................ | 510/112 |
| 2003/0100646 A1 * | 5/2003 | Anchor et al. ............. | 524/315 |
| 2005/0074467 A1 | 4/2005 | Fujita et al. | |
| 2005/0226841 A1 * | 10/2005 | Yu et al. .................... | 424/70.28 |
| 2007/0015710 A1 | 1/2007 | Chang et al. | |
| 2008/0057022 A1 | 3/2008 | Xia | |
| 2008/0096966 A1 * | 4/2008 | Burke et al. ................ | 514/561 |
| 2008/0194518 A1 | 8/2008 | Mookerjee et al. | |
| 2010/0087550 A1 | 4/2010 | Marlowe et al. | |

FOREIGN PATENT DOCUMENTS

| | | |
|---|---|---|
| JP | 2007-106727 A | 4/2007 |
| WO | 2008/049042 A2 | 4/2008 |

OTHER PUBLICATIONS

Cosmeticsinfo.org (Lauramide oxide: http://www.cosmeticsinfo.org/ingredient_details.php?ingredient_id=249.*
Gennaro, Alfonso. Remingtong's Pharmaceutical Sciences. Easton, PA: The Philadelphia College of Pharmacy and Science, 1985.*
Birnie et al., "Antimicrobial Evaluation of N-Alkyl Betaines and N-Alkyl-N,N-Dimethylamine Oxides with Variations in Chain Length," Antimicrobial Agents & Chemo, Sep. 2000, (vol. 44), (Issue. 9), (p. 2514-2517).

* cited by examiner

*Primary Examiner* — Jeffrey S Lundgren
*Assistant Examiner* — Chris Simmons
(74) *Attorney, Agent, or Firm* — Toan P. Vo

(57) ABSTRACT

An aqueous contact lens solution comprising less than 100 ppm of a tertiary amine oxide of general formula

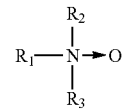

wherein $R_1$ is a $C_8$-$C_{18}$alkyl, and $R_2$ and $R_3$ are independently selected from a $C_1$-$C_4$alkyl or $C_1$-$C_4$hydroxyalkyl, and an antimicrobial component selected from the group consisting of biguanides, polymeric biguanides, quaternium ammonium compounds, hydrogen peroxide or a stabilized form of peroxide and any one mixture thereof. The solution has no anionic surfactant or less than 30 ppm of anionic surfactant. The invention is also directed to the use of the solution to clean and disinfect contact lenses, and in particular, soft, silicone, hydrogel contact lenses.

14 Claims, No Drawings

CONTACT LENS SOLUTION WITH A TERTIARY AMINE OXIDE

This application claims the benefit under 35 U.S.C. 119(e) of U.S. provisional application Ser. No. 61/108,920 filed Oct. 28, 2008.

The present invention relates to contact lens solutions with a tertiary amine oxide.

BACKGROUND OF THE INVENTION

During normal use, contact lenses become soiled or contaminated with a wide variety of compounds that can degrade lens performance. For example, a contact lens will become soiled with biological materials such as proteins or lipids that are present in the tear fluid and which adhere to the lens surface. Also, by handling of the contact lens, sebum (skin oil) or cosmetics or other materials can soil the contact lens. These biological and external contaminants can affect visual acuity and patient comfort. Accordingly, it is important to remove any debris from the lens surface for continued comfortable use with a lens care solution that contains one or more cleaning components.

Ophthalmic compositions formulated as a lens care solution must also contain one or more disinfectant components. Presently, the two most popular disinfectant components are poly(hexamethylene biguanide), at times referred to as PHMB or PAPB, and polyquaternium-1.

As stated, PHMB is presently used in contact, lens care solutions. These PHMB-based care solutions represent a significant improvement in patient comfort and antimicrobial effectiveness compared to most other antimicrobial components. However, as with any antimicrobial component there remains a tradeoff between the concentration of the antimicrobial component in the solution and the comfort experienced by the patient. Due to its wide commercial acceptance, extensive efforts have been directed to improve the antimicrobial efficacy or the comfort level to the patient by chemically modifying PHMB.

Another approach is to use two antimicrobial components, each at lower concentrations than if the two antimicrobial agents were to be used individually. The goal being that the two antimicrobial components would exhibit some form of a synergistic biocidal affect.

U.S. Pat. No. 5,840,671 describes a contact lens solution that contains a tertiary amine oxide and an anionic surfactant in the form of a triethanolamine salt. These two cleaning components are present in the solution at a total concentration from 0.1 wt. % to 20 wt. %. Also the weight ratio of the tertiary amine oxide to the anionic surfactant is from 1:4 to 30:1. It is said that the combination of the tertiary amine oxide with the anionic surfactant provide a "higher degree of cleaning effect than any cleaning solution which employs only one of those two kinds of surface active agents." Also, if the total amount of tertiary amine oxide and anionic surfactant is less than 0.1 wt. %, the lens solution "does not exhibit a satisfactory cleaning effect".

SUMMARY OF THE INVENTION

An aqueous contact lens solution comprising less than 100 ppm of a tertiary amine oxide of general formula

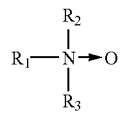

wherein $R_1$ is a $C_8$-$C_{18}$alkyl, and $R_2$ and $R_3$ are independently selected from a $C_1$-$C_4$alkyl or $C_1$-$C_4$hydroxyalkyl, and an antimicrobial component selected from the group consisting of biguanides, polymeric biguanides, quaternium ammonium compounds, hydrogen peroxide or a stabilized form of peroxide and any one mixture thereof. The solution has no anionic surfactant or less than 30 ppm of anionic surfactant. The solution is used to clean and disinfect contact lenses, and in particular, soft, silicone, hydrogel contact lenses.

DETAILED DESCRIPTION OF THE INVENTION

Applicants and others at Bausch & Lomb have developed and tested numerous ophthalmic formulations for use as lens care solutions. A lens care solution suitable for the lens care market must satisfy a number of functional characteristics. First, the solution must possess the cleaning ability to remove denatured tear proteins and tear lipids as well as other external contaminants. Second, the solution must possess significant disinfecting ability against a number of different bacteria and fungal strains. Third, the solution must remain comfortable to the contact lens patient with minimal stinging as well as provide a platform to provide additional comfort or protection to the ocular surface. Fourth, the solution must not cause significant shrinkage or swelling of the many different contact lens materials, which in turn can lead to loss in visual acuity and unwanted or pronounced lens movement.

In addition to all of the above characteristics, the solution must also pass a stringent test protocol that is referred by those in the art as "regimen" testing. An ophthalmic composition selectively formulated to clean and disinfect soft, silicone, hydrogel contact lenses must satisfy "regimen" testing for that formulation to obtain label approval from the Food and Drug Administration (FDA) as a no rub, contact lens cleaning and disinfecting solution. During development most of the tested solutions fail to pass the regimen test with each and every silicone hydrogel contact lens in the U.S. market. A more detailed description of the regimen test is provided under the sub-heading Examples in this application.

The invention is directed to an aqueous contact lens solution comprising less than 100 ppm of a tertiary amine oxide of general formula

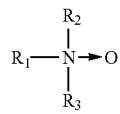

wherein $R_1$ is a $C_8$-$C_{18}$alkyl, and $R_2$ and $R_3$ are independently selected from a $C_1$-$C_4$alkyl or $C_1$-$C_4$hydroxyalkyl, and an antimicrobial component selected from the group consisting of biguanides, polymeric biguanides, quaternium ammonium compounds, hydrogen peroxide or a stabilized form of peroxide and any one mixture thereof. The solution has no anionic surfactant or less than 30 ppm of anionic surfactant.

The tertiary amine oxide is believed to complement the antimicrobial agent. In fact, relatively small amounts of tertiary amine oxide are needed to enhance the biocidal effectiveness of the solutions, particularly against fungi, e.g., *Fusarium solani* and *Candida albicans*. The lens care solutions will have less than 100 ppm of the tertiary amine oxide, or less than 60 ppm. In some instances, depending in-part on the type of tertiary amine oxide that is used, the concentrations of tertiary amine oxide in the solutions will be less than 30 ppm such as 10 ppm or 20 ppm.

As stated, the solutions will also include an antimicrobial component selected from quaternary ammonium compounds (including small molecules) and polymers and low and high molecular weight biguanides. For example, biguanides include the free bases or salts of alexidine, chlorhexidine, hexamethylene biguanides and their polymers (PHMB) and any one mixture thereof. The salts of alexidine and chlorhexidine can be either organic or inorganic and include gluconates, nitrates, acetates, phosphates, sulfates, halides and the like.

In a preferred embodiment, the solution will include a polymeric biguanide known as poly(hexamethylene biguanide) (PHMB or PAPB) commercially available from Zeneca, Wilmington, Del. under the trademark Cosmocil™ CQ. The PHMB is present in the compositions from 0.1 ppm to 2 ppm or from 0.2 ppm to 0.8 ppm.

Another biguanide of interest is 1,1'-hexamethylene-bis[5-(2-ethylhexyl)biguanide], which is referred to in the art as "alexidine". The alexidine is present in a solution from 0.5 ppm to 5 ppm or from 0.5 ppm to 2 ppm.

One of the more common quaternary ammonium compounds is α-[4-tris(2-hydroxyethyl)-ammonium chloride-2-butenyl]poly[1-dimethyl ammonium chloride-2-butenyl]-ω-tris(2-hydroxyethyl) ammonium chloride, also referred to in the art as polyquaternium-1. Quaternary ammonium compounds are generally referred to in the art as "polyquaternium" disinfectants, and are identified by a particular number following the designation such as polyquaternium-1, polyquaternium-10 or polyquaternium-42. Polyquaternium-1 is present in the lens care solutions from 0.5 ppm to 3 ppm. Polyquaternium-42 is also one of the more preferred polyquaternium disinfectants, see, U.S. Pat. No. 5,300,296. Polyquaternium-42 is present in the solutions from 5 ppm to 50 ppm.

It is to be understood by those in the art that the lens care solutions can include one or more of the antimicrobial components described above. For example, in one embodiment, a solution will include polyquaternium-1 in combination with a biguanide antimicrobial component such as poly(hexamethylene biguanide). The polyquaternium-1 is present in relatively low concentrations, that is, from 0.5 ppm to 3 ppm, relative to the reported concentration of polyquaternium-1 in both OPTI-FREE®EXPRESS and OPTI-FREE®REPLENISH. The polyquaternium-1, and the PHMB with the tertiary amine oxide, in combination, provide a multi-faceted disinfectant profile to enhance the biocidal efficacy of the lens care solutions.

In particular, the tertiary amine oxide complements the antimicrobial activity of hydrogen peroxide or stabilized-peroxide contact lens care solutions. The presence of the tertiary amine oxide in the lens care solution can function as an antimicrobial agent or preservative agent following neutralization of the hydrogen peroxide or stabilized-peroxide by either a solid support catalyst, e.g., a Pt-catalyst, or a chemical neutralizing agent, e.g., a dissolving tablet that contains catalase.

Contact Lens Care Solutions

The contact lens care solutions will very likely include a buffer system. By the terms "buffer" or "buffer system" is meant a compound that, usually in combination with at least one other compound, provides a buffering system in solution that exhibits buffering capacity, that is, the capacity to neutralize, within limits, either acids or bases (alkali) with relatively little or no change in the original pH. Generally, the buffering components are present from 0.05% to 2.5% (w/v) or from 0.1% to 1.5% (w/v).

The term "buffering capacity" is defined to mean the millimoles (mM) of strong acid or base (or respectively, hydrogen or hydroxide ions) required to change the pH by one unit when added to one liter (a standard unit) of the buffer solution. The buffer capacity will depend on the type and concentration of the buffer components. The buffer capacity is measured from a starting pH of 6 to 8.5, preferably from 7.4 to 8.4.

Borate buffers include, for example, boric acid and its salts, for example, sodium borate or potassium borate. Borate buffers also include compounds such as potassium tetraborate or potassium metaborate that produce borate acid or its salt in solutions. Borate buffers are known for enhancing the efficacy of certain polymeric biguanides. For example, U.S. Pat. No. 4,758,595 to Ogunbiyi et al. describes that a contact-lens solution containing PHMB can exhibit enhanced efficacy if combined with a borate buffer.

A phosphate buffer system preferably includes one or more monobasic phosphates, dibasic phosphates and the like. Particularly useful phosphate buffers are those selected from phosphate salts of alkali and/or alkaline earth metals. Examples of suitable phosphate buffers include one or more of sodium dibasic phosphate ($Na_2HPO_4$), sodium monobasic phosphate ($NaH_2PO_4$) and potassium monobasic phosphate ($KH_2PO_4$). The phosphate buffer components frequently are used in amounts from 0.01% or to 0.5% (w/v), calculated as phosphate ion.

Other known buffer compounds can optionally be added to the lens care compositions, for example, citrates, citric acid, sodium bicarbonate, TRIS, and the like. Other ingredients in the solution, while having other functions, may also affect the buffer capacity, e.g., propylene glycol or glycerin.

A preferred buffer system is based upon boric acid/borate, a mono and/or dibasic phosphate salt/phosphoric acid or a combined boric/phosphate buffer system. For example a combined boric/phosphate buffer system can be formulated from a mixture of boric acid/sodium borate and a monobasic/dibasic phosphate. In a combined boric/phosphate buffer system, the phosphate buffer is used (in total) at a concentration of 0.004 to 0.2 M (Molar), preferably 0.04 to 0.1 M. The borate buffer (in total) is used at a concentration of 0.02 to 0.8 M, preferably 0.07 to 0.2 M.

The lens care solutions can also include an effective amount of a surfactant component, a viscosity inducing or thickening component, a chelating or sequestering component, or a tonicity component. The additional component or components can be selected from materials which are known to be useful in contact lens care solutions and are included in amounts effective to provide the desired functional characteristic.

The amphoteric surfactants of general formula I are surface-active compounds with both acidic and alkaline properties and when used comprise 0.01 wt % to 1.0 wt % of the lens care solution. The amphoteric surfactants of general formula I include a class of compounds known as betaines. The betaines are characterized by a fully quaternized nitrogen atom and do not exhibit anionic properties in alkaline solutions, which means that betaines are present only as zwitterions at near neutral pH.

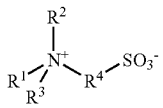

I wherein $R^1$ is R or —(CH$_2$),—NHC(O)R, wherein R is a $C_8$-$C_{16}$alkyl optionally substituted with hydroxyl and n is 2, 3 or 4; $R^2$ and $R^3$ are each independently selected from methyl, ethyl, propyl or iso-propyl; and $R^4$ is a $C_2$-$C_8$alkylene optionally substituted with hydroxyl.

All betaines are characterized by a fully quaternized nitrogen. In alkyl betaines, one of the alkyl groups of the quaternized nitrogen is an alkyl chain with eight to sixteen carbon atoms. One class of betaines is the sulfobetaines or hydroxysulfobetaines in which the carboxylic group of alkyl betaine is replaced by sulfonate. In hydroxysulfobetaines a hydroxygroup is positioned on one of the alkylene carbons that extend from the quaternized nitrogen to the sulfonate. In alkylamido betaines, an amide group is inserted as a link between the hydrophobic $C_8$-$C_{16}$alkyl chain and the quaternized nitrogen.

Certain sulfobetaines of general formula I are more preferred than others. For example, ZWITERGENT®3-10 available from Calbiochem Company, is a sulfobetaine of general formula I wherein $R^1$ is a straight, saturated alkyl with ten (10) carbons, $R^2$ and $R^3$ are each methyl and $R^4$ is —CH$_2$CH$_2$CH$_2$— (three carbons, (3)). Other sulfobetaines that can be used in the ophthalmic compositions include the corresponding ZWITERGENT®3-08 ($R^1$ is a straight, saturated alkyl with eight carbons), ZWITERGENT03-12 ($R^1$ is a straight, saturated alkyl with twelve carbons), Zwitergent®3-14 ($R^1$ is a straight, saturated alkyl with fourteen carbons) and ZWITERGENT®3-16 ($R^1$ is a straight, saturated alkyl with sixteen carbons). Accordingly, some of the more preferred the ophthalmic composition will include a sulfobetaine of general formula II wherein $R^1$ is a $C_8$-$C_{16}$alkyl and $R^2$ and $R^3$ is methyl.

In another embodiment, the amphoteric surfactant of general formula I is a hydroxysulfobetaine of general formula II

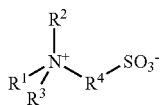

II wherein $R^1$ is a $C_8$-$C_{16}$alkyl substituted with at least one hydroxyl; $R^2$ and $R^3$ are each independently selected from methyl, ethyl, propyl or iso-propyl; and $R^4$ is a $C_2$-$C_8$alkylene substituted with at least one hydroxyl.

In another embodiment, the amphoteric surfactant is an alkylamido betaine of general formula III

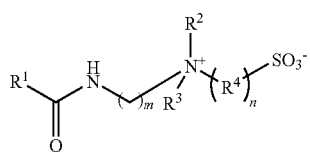

III wherein $R^1$ is a $C_8$-$C_{16}$alkyl, and m and n are independently selected from 2, 3, 4 or 5; $R^2$ and $R^3$ are each independently selected from a $C_1$-$C_4$alkyl optionally substituted with hydroxyl; and $R^4$ is a $C_2$-$C_8$alkylene optionally substituted with hydroxyl. The most common alkylamido betaines are alkylamidopropyl betaines, e.g., cocoamidopropyl dimethyl betaine and lauroyl amidopropyl dimethyl betaine.

Another preferred surfactant class are the nonionic surfactants. The surfactant should be soluble in the lens care solution and non-irritating to eye tissues. Many nonionic surfactants comprise one or more chains or polymeric components having oxyalkylene (—O—R—) repeats units wherein R has 2 to 6 carbon atoms. Preferred non-ionic surfactants comprise block polymers of two or more different kinds of oxyalkylene repeat units, which ratio of different repeat units determines the HLB of the surfactant. Satisfactory non-ionic surfactants include polyethylene glycol esters of fatty acids, e.g. coconut, polysorbate, polyoxyethylene or polyoxypropylene ethers of higher alkanes (C12-CIS). Examples of this class include polysorbate 20 (available under the trademark TWEEN® 20), polyoxyethylene (23) lauryl ether (BRIJ® 35), polyoxyethyene (40) stearate (MYRJ® 52), polyoxyethylene (25) propylene glycol stearate (ATLAS® G 2612). Still another preferred surfactant is tyloxapol.

A particular non-ionic surfactant consisting of a poly(oxypropylene)-poly(oxyethylene) adduct of ethylene diamine having a molecular weight from about 6,000 to about 24,000 daltons wherein at least 40 weight percent of said adduct is poly(oxyethylene) has been found to be particularly advantageous for use in cleaning and conditioning both soft and hard contact lenses. The CTFA Cosmetic Ingredient Dictionary's adopted name for this group of surfactants is poloxamine. Such surfactants are available from BASF Wyandotte Corp., Wyandotte, Mich., under TETRONIC®. Particularly good results are obtained with poloxamine 904, poloxamine 1107, poloxamine 1304 or anyone mixture of the three poloxamines. The foregoing poly(oxyethylene) poly(oxypropylene) block polymer surfactants will generally be present in a total amount from 0.0 to 2% w/v, from 0. to 1% w/v, or from 0.2 to 0.8% w/v.

One embodiment of particular interest is a lens care solution that specifically includes a poloxamine surfactant with a HLB value from 12 to 16.

An analogous of series of surfactants, for use in the lens care solutions, is the poloxamer series which is a poly(oxyethylene) poly(oxypropylene) block polymers available under PLURONIC® (commercially available form BASF). In accordance with one embodiment of a lens care composition the poly(oxyethylene)-poly(oxypropylene) block copolymers will have molecular weights from 2500 to 13,000 daltons or from 6000 to about 12,000 daltons. Specific examples of surfactants which are satisfactory include: poloxamer 108, poloxamer 188, poloxamer 237, poloxamer 238, poloxamer 288 and poloxamer 407. Particularly good results are obtained with poloxamer 237 or poloxamer 407. The foregoing poly(oxyethylene) poly(oxypropylene) block polymer surfactants will generally be present in a total amount from 0.0 to 2% w/v, from 0. to 1% w/v, or from 0.2 to 0.8% w/v.

The lens care solutions can also include one or more comfort or cushioning components. The comfort component can enhance and/or prolong the cleaning and wetting activity of the surfactant component and/or condition the lens surface rendering it more hydrophilic (less lipophilic) and/or to act as a demulcent on the eye. The comfort component is believed to cushion the impact on the eye surface during placement of the lens and serves also to alleviate eye irritation.

Suitable comfort components include, but are not limited to, water soluble natural gums, cellulose-derived polymers and the like. Useful natural gums include guar gum, gum tragacanth and the like. Useful cellulose-derived comfort components include cellulose-derived polymers, such as hydroxypropyl cellulose, hydroxypropylmethyl cellulose, carboxymethyl cellulose, methyl cellulose, hydroxyethyl cellulose and the like. A very useful comfort component is hydroxypropylmethyl cellulose (HPMC). Some non-cellulose comfort components include propylene glycol or glycerin. The comfort components are typically present in the solution from 0.01% to 1% (w/v).

One preferred comfort agent is hyaluronic acid, which is a linear polysaccharide (long-chain biological polymer) formed by repeating disaccharide units consisting of D-glucuronic acid and N-acetyl-D-glucosamine linked by $\beta(1-3)$ and $\beta(1-4)$ glycosidic linkages. Hyaluronic acid is distinguished from the other glycosaminoglycans, as it is free from covalent links to protein and sulphonic groups. Hyaluronic acid is ubiquitous in animals, with the highest concentration found in soft connective tissue. It plays an important role for both mechanical and transport purposes in the body; e.g., it gives elasticity to the joints and rigidity to the vertebrate disks, and it is also an important component of the vitreous body of the eye.

Hyaluronic acid is accepted by the ophthalmic community as a compound that can protect biological tissues or cells from compressive forces. Accordingly, hyaluronic acid has been proposed as one component of a viscoelastic ophthalmic composition for cataract surgery. The viscoelastic properties of hyaluronic acid, that is, hard elastic under static conditions though less viscous under small shear forces enables hyaluronic acid to basically function as a shock absorber for cells and tissues. Hyaluronic acid also has a relatively large capacity to absorb and hold water. The stated properties of hyaluronic acid are dependent on the molecular weight, the solution concentration, and physiological pH. At low concentrations, the individual chains entangle and form a continuous network in solution, which gives the system interesting properties, such as pronounced viscoelasticity and pseudoplasticity that is unique for a water-soluble polymer at low concentration.

The lens care solutions can include dexpanthenol, which is an alcohol of pantothenic acid, also called Provitamin B5, D-pantothenyl alcohol or D-panthenol. It has been stated that dexpanthenol may play a role in stabilizing the lachrymal film at the eye surface following placement of a contact lens on the eye. Dexpanthenol is preferably present in the solution in an amount from 0.2 to 5%/v, from 0.5 to 3% w/v, or from 1 to 2% w/v.

The contact lens care solutions can also include a sugar alcohol such as sorbitol or xylitol. Typically, dexpanthenol is used in combination with the sugar alcohol. The sugar alcohol is present in the lens care compositions in an amount from 0.4 to 5% w/v or from 0.8 to 3% w/v.

The contact lens care solutions can also include PG-alginate. PG-alginate is an ester of alginic acid, which is derived from sea kelp. A portion of the carboxyl groups are esterified with propylene glycol, and a portion are neutralized with an alkali.

The contact lens care solutions can also include ϵ-polylysine, which is a homo-polypeptide of about 25 to 30 l-lysine residues. The ϵ-polylysine can also provide an additional antimicrobial affect as it has been reported that ϵ-polylysine is absorbed electrostatically to the cell surface of the bacteria, followed by a stropping of the outer membrane and eventual disruption of the cytoplasm and cell death. Commercial sources of ϵ-polylysine are obtained from biofermentation of *Streptomyces* strains.

Another preferred comfort agent that is polyvinylpyrrolidone (PVP). PVP is a linear homopolymer or essentially a linear homopolymer comprising at least 90% repeat units derived from 1-vinyl-2-pyrrolidone monomer, the remainder of the monomer composition can include neutral monomer, e.g., vinyl or acrylates. Other synonyms for PVP include povidone, polyvidone, 1-vinyl-2-pyrrolidinone, and 1-ethenyl-2-pyrolionone. The PVP will preferably have a weight average molecular weight from 10,000 to 250,000 or from 30,000 to 100,000. Such materials are sold by various companies, including ISP Technologies, Inc. under the trademark PLASDONE®K-29/32, from BASF under the trademark KOLLIDON®, for example, KOLLIDON® K-30 or K-90. It is also preferred that one use pharmaceutical grade PVP.

The lens care solutions can also include one or more neutral or basic amino acids. The neutral amino acids include: the alkyl-group-containing amino acids such as alanine, isoleucine, valine, leucine and proline; hydroxyl-group-containing amino acids such as serine, threonine and 4-hydroxyproline; thio-group-containing amino acids such as cysteine, methionine and asparagine. Examples of the basic amino acid include lysine, histidine and arginine. The one or more neutral or basic amino acids are present in the compositions at a total concentration of from 0.1 to 3% w/v.

The lens care solutions can also include glycolic acid, asparatic acid or any mixture of the two at a total concentration of from 0.001% to 4% (w/v) or from 0.01% to 2.0% (w/v). In addition, the combined use of one or more amino acids and glycolic acid and/or asparatic acid can lead to a reduction in the change of the size of the contact lens due to swelling and shrinkage following placement in the lens solution.

The lens care solutions can also include one or more chelating components to assist in the removal of lipid and protein deposits from the lens surface following daily use. Typically, the ophthalmic compositions will include relatively low amounts, e.g., from 0.005% to 0.05% (w/v) of ethylenediaminetetraacetic acid (EDTA) or the corresponding metal salts thereof such as the disodium salt, $Na_2EDTA$. Other chelating components include citric acid and its salts or succinic acid and its salts.

The lens care solutions can also include a phosphonic acid, or its physiologically compatible salt, that is represented by the following formula:

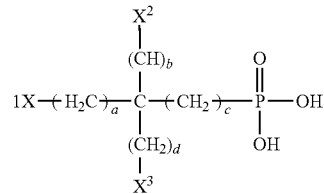

wherein each of a, b, c, and d are independently selected from integers from 0 to 4, preferably 0 or 1; $X^1$ is a phosphonic acid group (i.e., $P(OH)_2O$), hydroxy, amine or hydrogen; and $X^2$ and $X^3$ are independently selected from the group consisting of halogen, hydroxy, amine, carboxy, alkylcarbonyl, alkoxycarbonyl, or substituted or unsubstituted phenyl, and methyl. Exemplary substituents on the phenyl are halogen, hydroxy, amine, carboxy and/or alkyl groups. A particularly preferred species is that wherein a, b, c, and d in are zero, specifically the tetrasodium salt of 1-hydroxyethylidene-1,1-diphosphonic acid, also referred to as tetrasodium etidronate, commercially available from Monsanto Company as DEQUEST® 2016 diphosphonic acid sodium salt or phosphonate.

One possible alternative to the chelator Na₂EDTA or a possible combination with Na₂EDTA, is a disuccinate of formula IV below or a corresponding salt thereof;

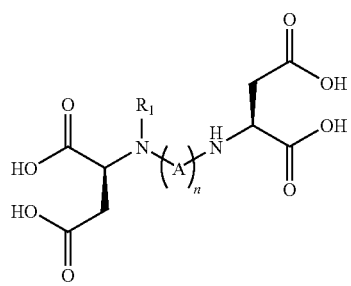

IV wherein $R_1$ is selected from hydrogen, alkyl or —C(O) alkyl, the alkyl having one to twelve carbons and optionally one or more oxygen atoms, A is a methylene group or an oxyalkylene group, and n is from 2 to 8. In one embodiment, the disuccinate is S,S-ethylenediamine disuccinate (S,S-EDDS) or a corresponding salt thereof. One commercial source of S,SEDDS is represented by OCTAQUEST® E30, which is commercially available from Octel. The chemical structure of the trisodium salt of S,S-EDDS is shown below. The salts can also include the alkaline earth metals such as calcium or magnesium. The zinc or silver salt of the disuccinate can also be used in the ophthalmic compositions.

Still another class of chelators include alkyl ethylenediaminetriacetates such as nonayl ethylenediaminetriacetate. See, U.S. Pat. No. 6,995,123 for a more complete description of such agents.

The lens care solutions will typically include an effective amount of a tonicity adjusting component. Among the suitable tonicity adjusting components that can be used are those conventionally used in contact lens care products such as various inorganic salts. Sodium chloride and/or potassium chloride and the like are very useful tonicity components. The amount of tonicity adjusting component is effective to provide the desired degree of tonicity to the solution.

The lens care solutions will typically have an osmolality in the range of at least about 200 mOsmol/kg for example, about 300 or about 350 to about 400 mOsmol/kg. The lens care solutions are substantially isotonic or hypertonic (for example, slightly hypertonic) and are ophthalmically acceptable.

Exemplary lens care solutions are formulated as a contact lens disinfecting solution prepared with the components and amounts of each listed in Table 1.

TABLE 1

| Component | minimum amount (wt. %) | maximum amount (wt. %) | preferred amount (wt. %) |
|---|---|---|---|
| boric acid | 0.10 | 1.0 | 0.64 |
| sodium borate | 0.01 | 0.20 | 0.1 |
| sodium chloride | 0.20 | 0.80 | 0.49 |
| C14 amine oxide (ppm) | 3 | 60 | 10 |
| TETRONIC ® 1107 | 0.05 | 2.0 | 1.00 |

TABLE 1-continued

| Component | minimum amount (wt. %) | maximum amount (wt. %) | preferred amount (wt. %) |
|---|---|---|---|
| Na₂EDTA | 0.005 | 0.15 | 0.03 |
| PHMB (ppm) | 0.2 | 2 | 1.3 |

Another contact lens solution includes the following ingredients listed in Table 2.

TABLE 2

| Component | minimum amount (wt. %) | maximum amount (wt. %) | preferred amount (wt. %) |
|---|---|---|---|
| sorbitol or xylitol | 0.5 | 5 | 3 |
| poloxamer 407 | 0.05 | 1.0 | 0.10 |
| sodium phosphate, dihydrogen | 0.10 | 0.8 | 0.46 |
| dexpanthenol | 0.01 | 1.0 | 0.03 |
| sorbitol | 0.1 | 1.0 | 0.4 |
| C14 amine oxide (ppm) | 3 | 60 | 15 |
| Na₂EDTA | 0.005 | 0.3 | 0.05 |
| PHMB (ppm) | 0.2 | 2 | 1 |

Another contact lens solution includes the following ingredients listed in Table 3.

TABLE 3

| Component | minimum amount (wt. %) | maximum amount (wt. %) | preferred amount (wt. %) |
|---|---|---|---|
| NaCl/KCl | 0.01 | 0.5 | 0.10 |
| sorbitol | 0.2 | 2.0 | 0.5 |
| propylene glycol | 0.2 | 2.0 | 0.6 |
| TETRONIC ®1304 | 0.01 | 0.2 | 0.05 |
| boric acid | 0.1 | 1.0 | 0.60 |
| sodium borate | 0.01 | 0.2 | 0.10 |
| hydroxypropyl guar | 0.01 | 0.5 | 0.05 |
| C14 amine oxide (ppm) | 5 | 40 | 15 |
| Na₂EDTA | 0.02 | 0.1 | 0.05 |
| polyquaternium-1 (ppm) | 1 | 10 | 6 |

As described, the lens care solutions can be used to clean and disinfect contact lenses. In general, the contact lens solutions can be used as a daily or every other day care regimen known in the art as a "no-rub" regimen. This procedure includes removing the contact lens from the eye, rinsing both sides of the lens with a few milliliters of solution and placing the lens in a lens storage case. The lens is then immersed in fresh solution for at least two hours. The lens is the removed form the case, optionally rinsed with more solution, and repositioned on the eye.

Alternatively, a rub protocol would include each of the above steps plus the step of adding a few drops of the solution to each side of the lens, followed by gently rubbing the surface between ones fingers for approximately 3 to 10 seconds. The lens can then be, optionally rinsed, and subsequently immersed in the solution for at least two hours. The lenses are removed from the lens storage case and repositioned on the eye.

The lens care solutions can be used with many different types of contact lenses including: (1) hard lenses formed from materials prepared by polymerization of acrylic esters, such as poly(methyl methacrylate) (PMMA), (2) rigid gas permeable (RGP) lenses formed from silicone acrylates and fluorosilicone methacrylates, (3) soft, hydrogel lenses, and (4) non-hydrogel elastomer lenses.

As an example, soft hydrogel contact lenses are made of a hydrogel polymeric material, a hydrogel being defined as a crosslinked polymeric system containing water in an equilibrium state. In general, hydrogels exhibit excellent biocompatibility properties, i.e., the property of being biologically or biochemically compatible by not producing a toxic, injurious or immunological response in a living tissue. Representative conventional hydrogel contact lens materials are made by polymerizing a monomer mixture comprising at least one hydrophilic monomer, such as (meth)acrylic acid, 2-hydroxyethyl methacrylate (HEMA), glyceryl methacrylate, N,N-dimethacrylamide, and N-vinylpyrrolidone (NVP). In the case of silicone hydrogels, the monomer mixture from which the copolymer is prepared further includes a silicone-containing monomer, in addition to the hydrophilic monomer. Generally, the monomer mixture will also include a crosslink monomer such as ethylene glycol dimethacrylate, tetraethylene glycol dimethacrylate, and methacryloxyethyl vinylcarbonate. Alternatively, either the silicone-containing monomer or the hydrophilic monomer may function as a crosslink agent.

The lens care solutions can also be formulated as a contact lens rewetting eye drop solution. By way of example, the rewetting drops may be formulated according to any one of the foregoing formulations of Tables 1 to 3 above. Alternatively, the formulations may be modified by increasing the amount of surfactant; by reducing the amount of antimicrobial agent to a preservative amount and/or by adding a humectant and/or demulcent.

EXAMPLES

Examples 1 to 5 and Comparative Example 1

Contact lens solutions of Examples 1 to 5 and Comparative Example 1 are listed in Table 4 are prepared using the following process (components are listed in wt. % unless noted in ppm). A volume of purified water equivalent to 85-90% of the total batch weight is added to a stainless steel mixing vessel. The following batch quantities of components are added to the water with stirring in the order listed: sodium chloride, edetate disodium, boric acid, sodium borate and poloxamine (Tetronics®). The solution is mixed (stirred) for not less than 10 minutes to ensure complete dissolution of each of the components. The pH of the resulting solution is measured at room temperature, and if necessary, the pH is adjusted with 1N NaOH or 1N HCl (target pH=7.5). The solution is then heat sterilized at 121° C. for at least 30 minutes.

In a second stainless steel vessel, a measured amount of PHMB or polyquaternium-1 (PQ-1) required for the batch is added to a given amount of purified water, and the solution is stirred for at least 10 minutes. The PHMB solution is aseptically transferred to the bulk solution through a sterilizing filter, and again the solution is stirred for at least 10 minutes. Purified water is then added to the bulk solution to bring to the batch weight reported in wt. % unless otherwise noted. The final solution is stirred for at least 15 minutes.

TABLE 4

|  | Example | | | | | Comp. |
| --- | --- | --- | --- | --- | --- | --- |
|  | 1 | 2 | 3 | 4 | 5 | Ex. 1 |
| boric acid | 0.80 | 0.45 | 0.64 | 0.45 | 0.45 | 0.45 |
| sodium borate | 0.16 | 0.40 | 0.09 | 0.15 | 0.15 | 0.40 |
| sodium chloride | 0.35 | 0.10 | 0.45 | 0.30 | 0.30 | 0.10 |
| $Na_2$EDTA | 0.02 | 0.05 | 0.02 | 0.02 | 0.02 | 0.05 |
| TETRONIC® 1304 | — | 0.40 | — | 0.4 | 0.4 | 0.40 |
| TETRONIC® 904 | 0.20 | — | 0.20 | — | — | — |
| propylene glycol | — | 0.5 | 0.20 | — | 0.40 | 0.5 |
| HPMC | — | — | — | 0.35 | — | — |
| glycerin | 0.40 | — | — | — | — | — |
| ZWITTERGENT® 3-10 | — | — | — | — | — | 0.10 |
| C12 amine oxide (ppm) | 50 | — | — | — | — | — |
| C14 amine oxide (ppm) | — | 20 | 7 | 15 | 10 | — |
| PHMB (ppm) | 0.70 | 1.0 | 0.7 | 1.0 | — | 1.0 |
| Polyquaternium-1 (ppm) | — | — | — | — | 8 | — |

Biocidal Stand-Alone Stability

In order to assess the activity of the formulation, samples are bottled in 4 oz PET containers and stored at ambient temperature, as well as elevated temperatures for a given period. The stand-alone biocidal efficacy of the samples is tested at designated intervals to determine the stability of the formulation with time for is disinfection activity. The "Stand-Alone Procedure for Disinfecting Products" is based on the Disinfection Efficacy Testing for Products dated May 1, 1997, prepared by the U.S. Food and Drug Administration, Division of Ophthalmic Devices. This performance requirement does not contain a rub procedure.

The stand-alone test challenges a disinfecting product with a standard inoculum of a representative range of microorganisms and establishes the extent of viability loss at predetermined time intervals comparable with those during which the product may be used. The primary criteria for a given disinfection period (corresponding to a potential minimum recommended disinfection period) is that the number of bacteria recovered per mL must be reduced by a mean value of not less than 3.0 logs within the given disinfection period. The number of mold and yeast recovered per ml must be reduced by a mean value of not less than 1.0 log within the minimum recommended disinfection time with no increase at four times the minimum recommended disinfection time.

The antimicrobial efficacy of each of the various compositions for the chemical disinfection and cleaning of contact lenses are evaluated in the presence of 10% organic soil using the stand-alone procedure. Microbial challenge inoculums are prepared using *Staphylococcus aureus* (ATCC 6538), *Pseudomonas aeruginosa* (ATCC 9027), *Serratia marcescens* (ATCC 13880), *Candida albicans* (ATCC 10231) and *Fusarium* solani (ATCC 36031). The test organisms are cultured on appropriate agar and the cultures are harvested using sterile Dulbecco's Phosphate Buffered Saline plus 0.05 percent weight/volume polysorbate 80 (DPBST) or a suitable diluent and transferred to a suitable vessel. Spore suspensions are filtered through sterile glass wool to remove hyphal fragments. *Serratia marcescens*, as appropriate, is filtered through a 1.2 μm filter to clarify the suspension.

After harvesting, the suspension is centrifuged at no more than 5000×g for a maximum of 30 minutes at a temperature of 20° C. to 25° C. The supernatant is decanted and resuspended in DPBST or other suitable diluent. The suspension is centrifuged a second time, and resuspended in DPBST or other suitable diluent. All challenge bacterial and fungal cell suspensions are adjusted with DPBST or other suitable diluent to $1\times10^7$ to $1\times10^8$ cfu/mL. The appropriate cell concentration may be estimated by measuring the turbidity of the suspension, for example, using a spectrophotometer at a preselected wavelength, for example, 490 nm. One tube is prepared containing a minimum of 10 mL of test solution per challenge organism. Each tube of the solution to be tested is inoculated with a suspension of the test organism sufficient to provide a final count of $1\times10^5$ to $1\times10^6$ cfu/mL, the volume of the inoculum not exceeding 1 percent of the sample volume. Dispersion of the inoculum is ensured by vortexing the sample for at least 15 seconds. The inoculated product is stored at 10° C. to 25° C. Aliquots in the amount of 1.0 mL are taken of the inoculated product for determination of viable counts after certain time periods of disinfection.

The suspension is mixed well by vortexing vigorously for at least 5 sec. The 1.0 mL aliquots removed at the specified time intervals are subjected to a suitable series of decimal dilutions in validated neutralizing media. The suspensions are mixed vigorously and incubated for a suitable period of time to allow for neutralization of the microbial agent. The viable count of organisms is determined in appropriate dilutions by preparation of triplicate plates of trypticase soy agar (TSA) for bacteria and Sabouraud dextrose agar (SDA) for mold and yeast. The bacterial recovery plates are incubated at 30° C. to 35° C. for two to four days. The yeast recovery plates are incubated at 20° C. to 30° C. for two to four days. The mold recovery plates are incubated at 20° C. to 25° C. for three to seven days. The average number of colony forming units is determined on countable plates. Countable plates refer to 30 to 300 cfu/plates for bacteria and yeast, and 8 to 80 cfu/plate for mold except when colonies are observed only for the $10^0$ or $10^{-1}$ dilution plates. The microbial reduction is then calculated at the specified time points.

In order to demonstrate the suitability of the medium used for growth of the test organisms and to provide an estimation of the initial inoculum concentration, inoculum controls are prepared by dispersing an identical aliquot of the inoculum into a suitable diluent, for example, DPBST, using the same volume of diluent used to suspend the organism as listed above. Following inoculation in a validated neutralizing broth and incubation for an appropriate period of time, the inoculum control must be between $1.0\times10^5$ and $1.0\times10^6$ cfu/mL.

Biocidal stand-alone stability data was obtained with Example 3 and is listed in Table 5.

TABLE 5

Four-hour biocidal stability in PET bottle at elevated temperatures for Example 3.

| Time point | Temp ° C. | Sa | Pa | Sm | Ca | Fs |
|---|---|---|---|---|---|---|
| $t_0$ | 25 | >4.9 | >4.7 | 4.7 | 1.5 | 2.0 |
| two weeks | 25 | 4.8 | >4.5 | 3.8 | 1.5 | 2.4 |
|  | 40 | 4.3 | >4.5 | 3.9 | 1.7 | 2.9 |
| one month | 25 | 4.5 | >4.6 | 4.2 | 2.0 | 2.1 |
|  | 40 | 4.9 | 4.6 | 4.2 | 1.9 | 2.3 |
| two month | 25 | >4.6 | >4.6 | 4.5 | 2.8 | 2.8 |
|  | 40 | 3.8 | 3.6 | 3.7 | 2.5 | 3.0 |
| three month | 25 | 5.0 | 4.8 | NT | 2.4 | 2.7 |
|  | 40 | >5.0 | >4.8 | 3.5 | 2.2 | 2.6 |

NT—not tested

Regimen Testing with PureVision® Lenses

Regimen efficacy testing involves first inoculating both sides of the contact lenses with 0.01 mL of a suspension of $1.0\times10^7$-$1.0\times10^8$ CFU/mL of the test organism in organic soil solution. The inoculum is allowed to adsorb to each lens for 5-10 minutes at 20-25° C. After the absorption period, each side of the lenses are rinsed for 5 seconds with the test solution and then allowed to soak in the test solution stored in standard B&L lens cases for 4 hours. To recover the surviving challenged organisms, a given volume of validated neutralizing medium is placed in a filtration apparatus. The entire contents of a given lens case (lens and test solution) is transferred to the neutralizing medium in the filtration apparatus. After an appropriate neutralization exposure time, a vacuum is applied to the filtration apparatus to filter the solution. The lens is aseptically transferred to a bed of agar medium appropriate for the recovery of the test organism. A given amount of the same agar (at 40-50° C.) used in the bed is poured over the lens to cast it. The test filter is placed on the surface of agar medium appropriate to recover the test organism. Bacteria recovery plates are incubated for 2-4 days at 30-35° C., while yeast recovery plates are incubated for 3-5 days at 20-25° C. or 30-35° C. and mold recovery plates are incubated for 3-7 days at 20-25° C. Appropriate inoculum, lens inoculum, as well as, neutralizing and recovery controls are run for each experiment.

The regimen efficacy of Example 3 was tested as described in the above paragraph against *Candida albicans*, which is typically the most resistant microbe for the test. Example 3 passed Regimen testing.

Lens Compatibility Testing

TABLE 7

30 Cycle lens compatibility data of commercial lenses with Example 3.

| Soft Contact Lens Type | Parameter | ISO Spec | 30 Cycles | Reverse 30 Cycles |
|---|---|---|---|---|
| ACUVUE ® 2 | Diameter | ±0.20 mm | In spec | In spec |
|  | Estimated Base Curve | ±0.20 mm | In spec | In spec |
| SOFTLENS ® 66 TORIC | Diameter | ±0.20 mm | In spec | In spec |
|  | Estimated Base Curve | ±0.20 mm | In spec | In spec |
| SOFTLENS ® 38 | Diameter | ±0.20 mm | In spec | In spec |
|  | Estimated Base Curve | ±0.20 mm | In spec | In spec |
| ACUVUE ® ADVANCE | Diameter | ±0.20 mm | In spec | In spec |
|  | Estimated Base Curve | ±0.20 mm | In spec | In spec |
| ACUVUE ® OASYS | Diameter | ±0.20 mm | In spec | In spec |
|  | Estimated Base Curve | ±0.20 mm | In spec | In spec |
| NIGHT & DAY ® | Diameter | ±0.20 mm | In spec | In spec |
|  | Estimated Base Curve | ±0.20 mm | In spec | In spec |
| O$_2$OPTIX ™ | Diameter | ±0.20 mm | In spec | In spec |
|  | Estimated Base Curve | ±0.20 mm | In spec | In spec |
| PUREVISION ® | Diameter | ±0.20 mm | In spec | In spec |
|  | Estimated Base Curve | ±0.20 mm | In spec | In spec |

TABLE 7-continued

30 Cycle lens compatibility data of commercial lenses with Example 3.

| Soft Contact Lens Type | Parameter | ISO Spec | 30 Cycles | Reverse 30 Cycles |
|---|---|---|---|---|
| BIOFINITY ® | Diameter | ±0.20 mm | In spec | In spec |
|  | Estimated Base Curve | ±0.20 mm | In spec | In spec |

We claim:

1. An aqueous contact lens cleaning and disinfecting solution comprising 10 ppm to 100 ppm of a tertiary amine oxide of general formula

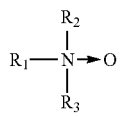

i)

wherein $R_1$ is a $C_8$-$C_{18}$ alkyl, and $R_2$ and $R_3$ are independently selected from a $C_1$-$C_4$ alkyl or $C_1$-$C_4$ hydroxyalkyl, and an antimicrobial component selected from the group consisting of biguanides, polymeric biguanides, quaternium ammonium compounds, hydrogen peroxide or a stabilized form of peroxide and any one mixture thereof, wherein the solution has no anionic surfactant or less than 30 ppm of anionic surfactant.

2. The solution of claim 1 wherein the antimicrobial component is α-[4 tris(2-hydroxyethyl)-ammonium chloride-2-butenyl]poly[1-dimethyl ammonium chloride-2-butenyl]-ω-tris(2-hydroxyethyl) ammonium chloride, which is present from 1 ppm to 10 ppm.

3. The solution of claim 1 further comprising dexpanthenol, sorbitol, glycolic acid, 2-amino-2-methyl-1,3-propanediol, propylene glycol or any one mixture thereof.

4. The solution of claim 1 wherein the tertiary amine oxide is present at a concentration of less than 60 ppm.

5. The solution of claim 2 wherein the tertiary amine oxide is myristamine oxide or lauramine oxide.

6. The solution of claim 1 further comprising 0.01 wt. % to 1.0 wt. % of an amphoteric surfactant of general formula I

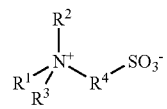

I wherein $R^1$ is R or —$(CH_2)_n$—NHC(O)R, wherein R is a $C_8$-$C_{16}$ alkyl optionally substituted with hydroxyl and n is 2, 3 or 4; $R^2$ and $R^3$ are each independently selected from methyl, ethyl, propyl or iso-propyl; and $R^4$ is a $C_2$-$C_8$ alkylene optionally substituted with hydroxyl.

7. The solution of claim 1 further comprising hydroxypropyl guar or hydroxypropylmethyl cellulose.

8. The solution of claim 2 further comprising a poloxamine surfactant with a HLB value from 12 to 16.

9. The solution of claim 1 wherein the antimicrobial component is poly(hexamethylene biguanide), which is present from 0.1 ppm to 2.0 ppm.

10. The solution of claim 9, wherein the tertiary amine oxide is myristamine oxide or lauramine oxide.

11. The solution of claim 9, comprising 0.8 ppm to 1.3 ppm of poly(hexamethylene biguanide); and further comprising
 a borate phosphate buffer system;
 a nonionic surfactant selected from poloxamer, poloxamine or any combination thereof; and
 sufficient sodium chloride, potassium chloride or any combination thereof to provide the solution with an osmolality of from 200 mOsmol/kg to 400 mOsmol/kg.

12. The solution of claim 11, wherein the tertiary amine oxide is myristamine oxide or lauramine oxide.

13. A method of cleaning and disinfecting a contact lens, the method comprising soaking the contact lens in the solution of claim 1 for at least two hours.

14. The method of claim 13, further comprising inserting the cleaned and disinfected contact lens into the eye without rinsing the lens after soaking.

* * * * *